(12) United States Patent
Kim et al.

(10) Patent No.: US 8,048,048 B2
(45) Date of Patent: Nov. 1, 2011

(54) METHOD AND SYSTEM FOR MEASURING URINARY FLOW RATE

(75) Inventors: Kyung Ah Kim, Cheongju (KR); Eun Jong Cha, Cheongju (KR); Seong Su Choi, Cheongju (KR)

(73) Assignee: Chungbuk National University Industry Academic Corporation Foundation, Cheongju-si, Chungcheongbuk-Do (KP)

( * ) Notice: Subject to any disclaimer, the term of this patent is extended or adjusted under 35 U.S.C. 154(b) by 224 days.

(21) Appl. No.: 12/332,896

(22) Filed: Dec. 11, 2008

(65) Prior Publication Data

US 2010/0152684 A1    Jun. 17, 2010

(51) Int. Cl.
*A61M 1/00*    (2006.01)
*A61B 5/00*    (2006.01)
*B65D 81/00*   (2006.01)
*G01F 1/05*    (2006.01)

(52) U.S. Cl. ........ 604/322; 600/573; 600/584; 604/318; 604/325; 73/223; 73/861.71

(58) Field of Classification Search .................. 604/325, 604/318, 322; 600/573, 584; 73/223, 861.71
See application file for complete search history.

(56) References Cited

U.S. PATENT DOCUMENTS
2010/0064797 A1 * 3/2010 Hirao .............................. 73/198

FOREIGN PATENT DOCUMENTS
WO    WO 2007/111001 A1 * 10/2007
* cited by examiner

*Primary Examiner* — Max Hindenburg
*Assistant Examiner* — Emily Lloyd
(74) *Attorney, Agent, or Firm* — Greer, Burns & Crain, Ltd.

(57) ABSTRACT

A method and system for measuring a urinary flow rate minimizes impact noise caused by urine to measure the urinary flow rate using a plurality of load cells when prostatic hypertrophy is diagnosed. The method includes measuring an amount of urine collected into a container using a plurality of load cells, extracting and averaging urinary flow rate signals from the measured results, and removing the impact noise from the urinary flow rate signals, converting the urinary flow rate signals into digital signals through an A/D converting circuit, and outputting the digital signals using a personal computer or a microprocessor analyzer which is interfaced with the A/D converting circuit.

4 Claims, 5 Drawing Sheets

[Fig 1]
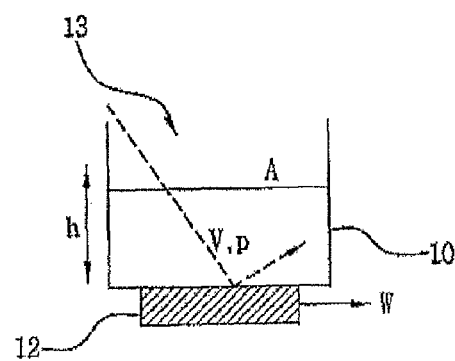
[Fig 2]
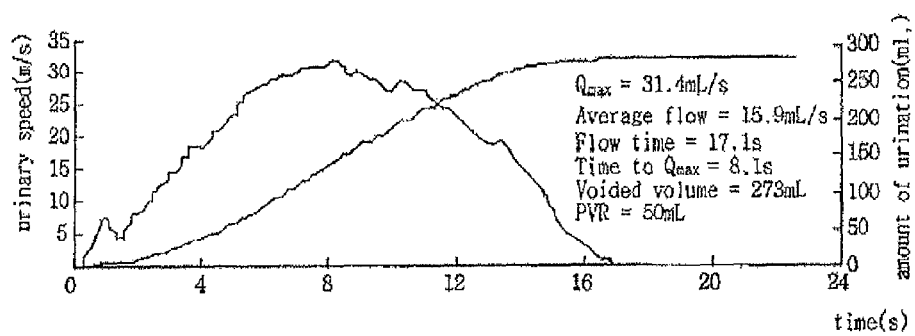

[Fig 3]
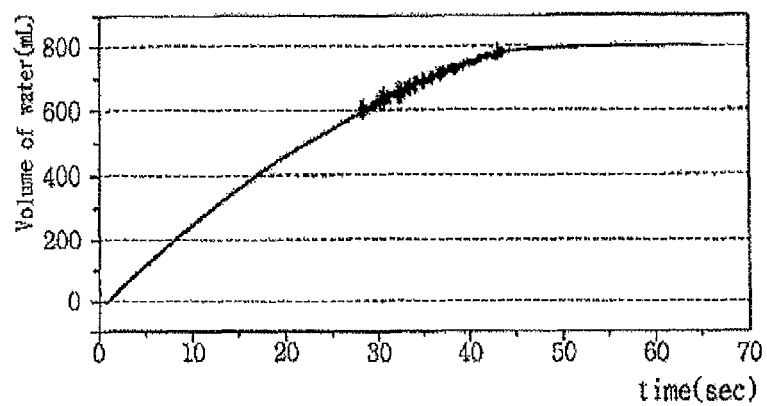
[Fig 4]
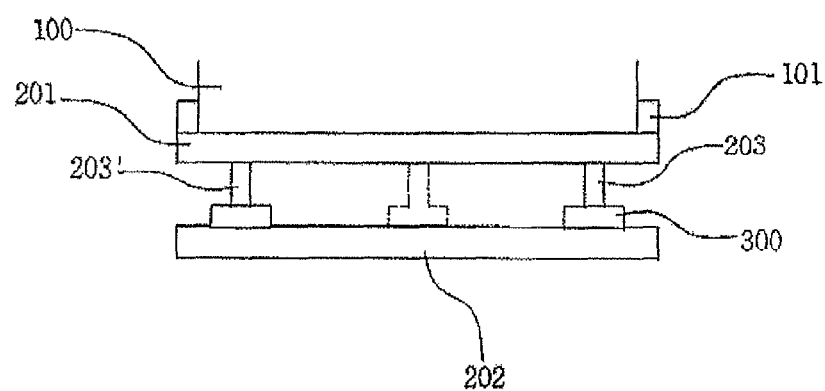

[Fig 5]
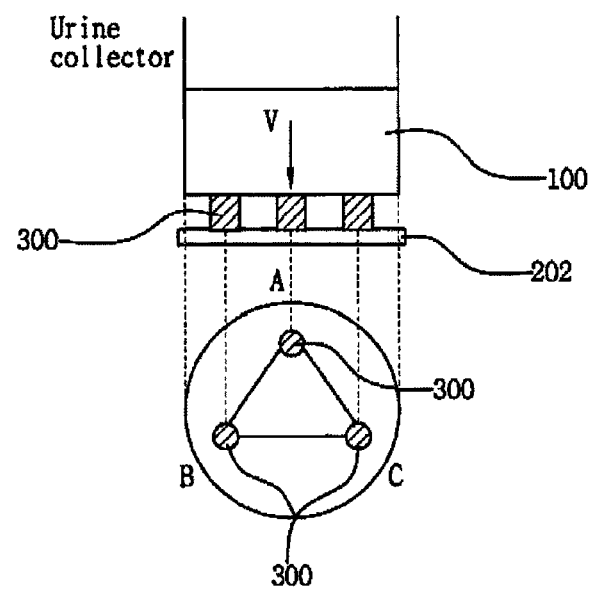
[Fig 6]
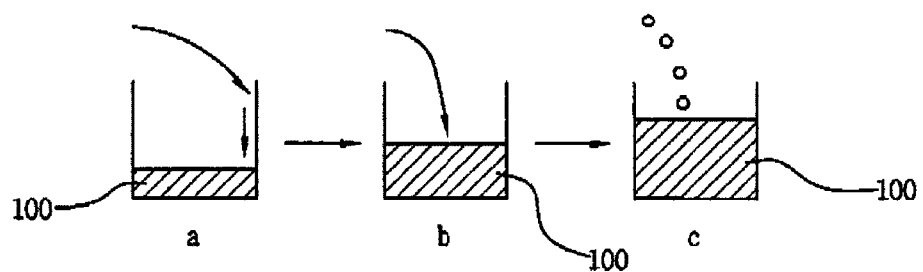

METHOD AND SYSTEM FOR MEASURING URINARY FLOW RATE

BACKGROUND OF THE INVENTION

1. Field of the Invention

The present invention relates to a method and system for measuring a urinary flow rate, and more particularly to a method and system for measuring a urinary flow rate, in which impact noise caused by urine is minimized to measure the urinary flow rate using a plurality of load cells.

2. Description of the Prior Art

Men discharge urine through the urethra encircled by the prostate gland located under the bladder. In detail, the prostate gland is found only in the male, and refers to a glandular reproductive organ that has chestnut-shaped soft tissue under the bladder with weight of about 20 g and encircles the urethra. The prostate gland is hypertrophied by, for instance, prostatitis, which is called prostatic hypertrophy. This disease is one of the representative chronic diseases of an aged society with which about 50% to 80% of adult men, particularly men in the fifties or more, are attacked. When this prostatic hypertrophy occurs, the urethra encircled by the prostate gland is compressed to cause abnormal urination as well as sexual dysfunction.

A method of determining whether or not the prostate gland is abnormal; namely whether or not prostatic hypertrophy exists, as described above, by employing uroflowmetry that continuously measures a urinary flow rate signal indicating an amount of urine per unit time during urination. This method is an indispensable biomedical test in the event of diagnosis of the prostatic hypertrophy.

The conventional uroflowmetry is typically based on measurement of the weight of urine. As schematically illustrated in FIG. 1, urine 13 is collected into a container 10 having a predetermined diameter, and a load cell device, i.e. a weight sensor, which is mounted under the container 10 and measures a weight of urine, is situated. A change in the weight (mass) of urine is measured during urination. This method is based on the principle that the weight W measured by the weight sensor 12 is proportional to a volume V of urine collected into the container 10. For example, assuming that the weight of urine represented by the weight sensor 12 be W, that the volume of urine collected into the container 10 be V, that a cross section of the container be A, that a density of urine be $\rho$, and that a height of urine collected into the container 10 be h, the weight W is expressed by the following equation.

$$W = \rho g A h.$$

Here, the product of the cross section A of the container and the height h of urine equal to the volume V of urine, the equation is as follows.

$$W = \rho g A h = \rho g V$$

Here, the density $\rho$ of urine is nearly equal to water, and thus is regarded as 1, and g is the gravitational constant. The equivalent equation can be expressed as follows.

$$W = \rho g A h = \rho g V \propto V$$

Accordingly, the change in the volume of urine can be found by measuring the change in the weight of urine collected during urination. However, a biological variable that is to be actually calculated in order to determine whether or not the prostate gland is abnormal is a urinary flow rate signal, and thus a method of calculating the change in the volume of urine into the urinary flow rate signal is used. In other words, since the urinary flow rate is defined as a rate of change in volume over time, a weight signal proportional to the volume is differentiated with respect to time, and thereby the urinary flow rate is yielded.

An example of carrying out the uroflowmetry using the conventional method is shown in the graph of FIG. 2.

In detail, FIG. 2 shows the results of the conventional uroflowmetry along with a volume signal obtained by measuring the weight of urine of a normal person, a urinary flow rate signal differentiating the volume signal, and various diagnosis parameters obtained by analysis. (Textbook of Voiding Dysfunction and Female Urology, Korean Continence Society, Il-Jo-Gak, 331 p, 2003).

In the conventional method and apparatus for the uroflowmetry as described above, the urinary flow rate is tested by continuously measuring a change in weight of urine using the weight sensor during collecting the urine into the container, and analyzing the volume signal based on the measurement, the urinary flow rate signal differentiating the volume signal, and so on.

However, in the conventional method and apparatus, when the urine 13 is collected into the container 10 during urination, a stream of urine (dotted line of FIG. 1) directly touches the bottom of the container 10, and thus the bottom of the container 10 gets an additional impact due to momentum (mass×velocity) of the stream of urine in addition to the weight of urine. Thus, in addition to the weight of urine, impulse of urine is transmitted to the weight sensor 12. An effect of the impact is randomly transmitted to the weight sensor 12 according to amount and velocity of the stream of urine, and thus acts as measurement noise. Further, since the urine is not contracted or expanded like gas, there is no damping action. As such, after the urine is collected at a predetermined amount, the impulse applied to a surface of the urine is transmitted intact to the weight sensor 12 under the bottom of the container 10. This leads to a decrease in reliability when the differentiation and the diagnosis parameters for obtaining the urinary flow rate are calculated.

FIG. 3 is a graph showing the results of test measurement based on a conventional method for uroflowmetry, in which the test is done by pouring water of 800 ml instead of the urine like urination, and measuring a weight of water to obtain a volume signal. It can be found that the measurement noise exists throughout the volume signal. In order to prevent this impact effect, the water is adapted to flow down along a wall of the container, thereby minimizing the impulse. To this end, a separate funnel is typically used. Thus, the separate funnel must be precisely designed and manufactured so as to be fitted to the collecting container, and then be inserted into the collecting container, which is troublesome.

SUMMARY OF THE INVENTION

Accordingly, the present invention has been made keeping in mind the above problems occurring in the prior art, and embodiments of the present invention provide a method and system for measuring a urinary flow rate, capable of minimizing impact noise when an amount (volume or weight) of urine is measured.

In an embodiment of the present invention, there is provided a method for measuring a urinary flow rate so as to minimize impact noise when prostatic hypertrophy is diagnosed. The method comprises the steps of: measuring an amount of urine collected into a container using a plurality of load cells; extracting and averaging urinary flow rate signals from the measured results, and removing the impact noise from the urinary flow rate signals; converting the urinary flow rate signals into digital signals through an A/D converting circuit; and outputting the digital signals using a personal computer or a microprocessor analyzer which is interfaced with the A/D converting circuit.

In another embodiment of the present invention, there is provided a system for measuring a urinary flow rate so as to minimize impact noise when prostatic hypertrophy is diagnosed. The system comprises: a container into which urine is collected; an upper plate on which the container is placed; a plurality of load cells installed below the upper plate and attached to a bottom plate; an extracting and averaging circuit extracting and averaging urinary flow rate signals from the load cells; an A/D converting circuit receiving the signals from the extracting and averaging circuit, and performing A/D conversion on the received signals; and a personal computer or a microprocessor analyzer outputting the signals from the A/D converting circuit.

In another embodiment, the load cells may number three and be disposed in an equilateral triangular pattern.

BRIEF DESCRIPTION OF THE DRAWINGS

The above and other objects, features and other advantages of the present invention will be more clearly understood from the following detailed description when taken in conjunction with the accompanying drawings, in which:

FIG. 1 is a conceptual view illustrating a conventional method for uroflowmetry;

FIG. 2 is a graph illustrating the results of conventional uroflowmetry performed on a normal person;

FIG. 3 is a graph showing the results of test measurement based on a conventional method for uroflowmetry;

FIG. 4 is a schematic view illustrating the part of a system for measuring a urinary flow rate according to an embodiment of the present invention;

FIG. 5 is a schematic view illustrating positions of load cells used in a system for measuring a urinary flow rate according to an embodiment of the present invention;

FIG. 6 is a conceptual view illustrating urination simulation made using water;

DETAILED DESCRIPTION OF THE INVENTION

Figure 7A:
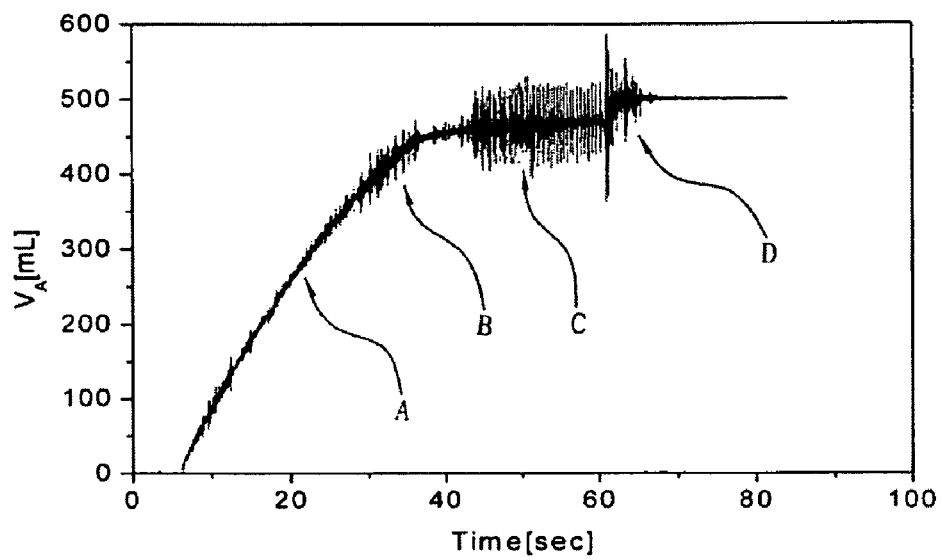
FIG. 7a, 7b and 7c are graphs for urinary flow rate signals measured by load cells according an embodiment of the present invention.

Reference will now be made in greater detail to exemplary embodiments of the invention with reference to the accompanying drawings.

As described in the Description of the Related Art section, the load cell for measuring the weight collected into the urinary container gets the weight as well as the impulse of urine. In detail, the urinary flow rate signal measured by the load cell is composed of the sum of the volume signal v proportional to the weight of urine and the impact noise e. Here, the volume signal v shows a tendency to gradually increase during urination, while the impact noise e is a noise component randomly varied according to urination circumstances. Generally, the random noise component is measured several times, and then the measured noise components are calculated on the average. Thereby, the noise components offset each other. This is called a repeated measurement principle that is generally used.

Thus, as for a method used in an embodiment of the present invention on the basis of the repeated measurement principle, three small load cells instead of one large load cell are installed under the urinary container in an equilateral triangular pattern, the urinary flow rate signals measured by the small load cells are averaged to minimize the noise, particularly the impact noise e. Under ideal circumstances, the components of the noise e offset each other, and thus will be zero (0). Accordingly, the method allows the urinary flow rate to be accurately measured.

First, FIG. 4 schematically illustrates positions of load cells in a system for measuring a urinary flow rate according to an embodiment of the present invention. In an embodiment of the present invention, a urine collecting container 100 is located between urine collecting container supports 101. A plurality of load cells 300 is interposed between an upper plate 201 and a bottom plate 202. The load cells 300 are attached to the bottom plate 202. The upper plate 201 is provided with supports 203 and 203' thereunder so as to press down the centers of the load cells 300. The load cells 300 are installed so as to form an equilateral triangle within the bottom plate 202. In other words, as illustrated in FIG. 5, the three load cells 300 (A, B and C) have an equilateral triangular pattern when installed, and are connected with a typical measurement meter.

In FIG. 5, a total weight (or volume) V of urine collected into the container 100 is equal to the sum of weights applied to the load cells A, B and C, namely $V=V_A+V_B+V_C$, because each load cell measures the weight of V/3 when the weight of urine is vertically applied. Here, the weight of urine applied to each load cell will additionally receive impact noise, measurement noise e, as follows:

$$V_A = \frac{V}{3}e_A, \; V_B = \frac{V}{3}e_B, \text{ and } V_C = \frac{V}{3}e_C$$

Here, if the impact noise components $e_A$, $e_B$ and $e_C$ are complete random signals, their sum, $e_A+e_B+e_C$, will be zero (0). Thus, the measurement noise can be minimized by summing up $V_A$, $V_B$ and $V_C$.

In order to verify a measurement noise effect by putting into practice the embodiment of the present invention on the basis of the above-mentioned principle, urination simulation is made using water as illustrated in FIG. 6. An outlet of the container is provided with an outlet in a sidewall thereof. Thus, the water cannot be completely discharged up to the bottom of the container, and thus the remaining water is manually discharged. The urinary flow rate signals measured by the three load cells are graphically shown in FIGS. 7a, 7b and 7c.

FIG. 6a shows that a stream of urine (arrow) is collected along the sidewall of the collecting container 100, FIG. 6b shows that the stream of urine becomes weak with the lapse of time, and then deflects from the sidewall of the container to fall into a surface of the collected urine, and FIG. 6c shows that the stream of urine falls in drops.

Figure 7B:
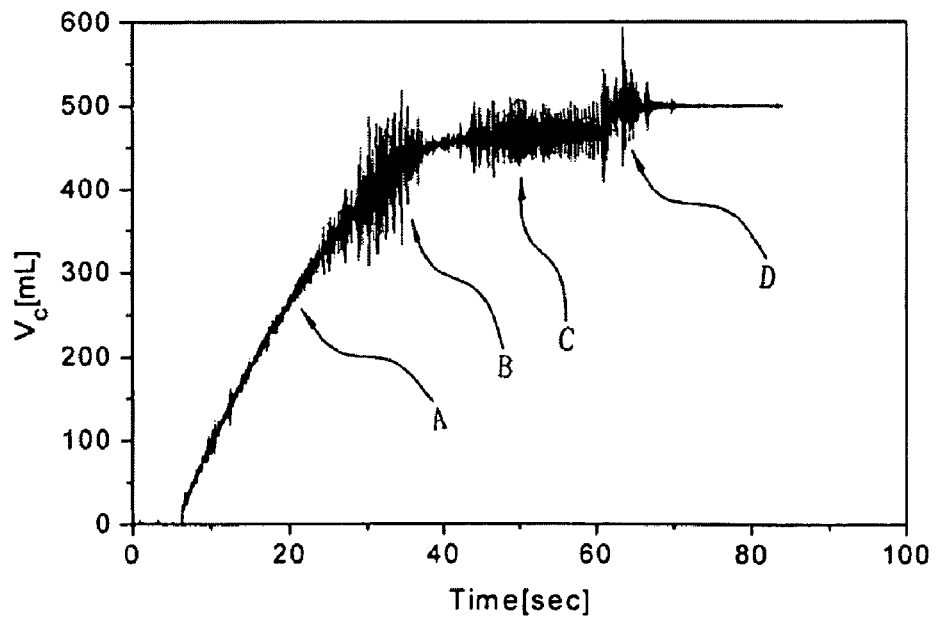
Figure 7C:
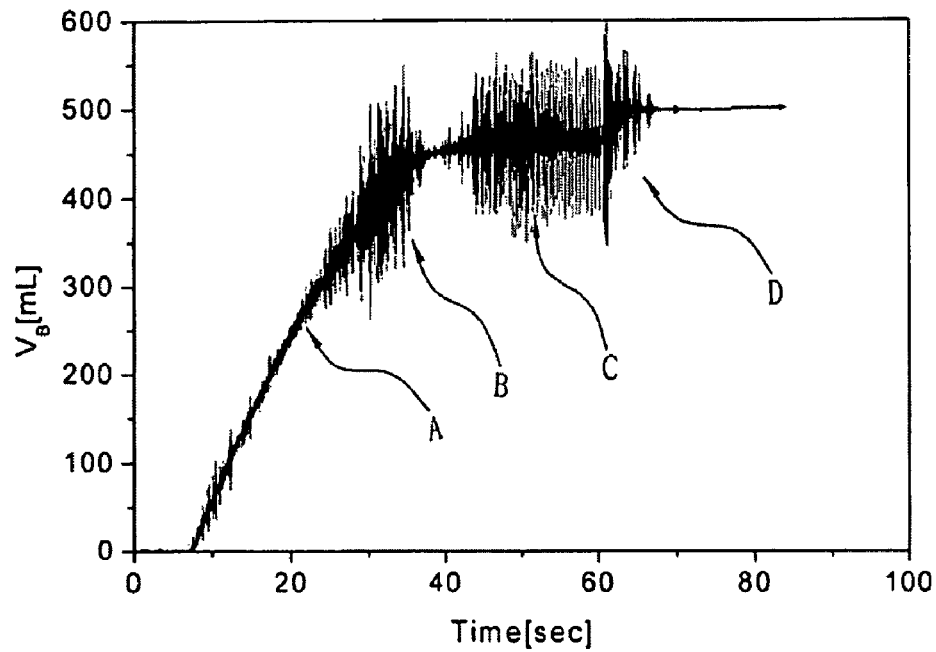

As a result of the measurement, as illustrated in FIGS. 7a, 7b and 7c, it can be found that the urinary flow rate signals measured from the respective three load cells are accompanied with a considerable level of impact noise. In detail, the urinary flow rate signal A when the stream of urine is collected along the sidewall of the container has the impact noise lower than that B when the stream of urine is collected apart from the sidewall of the container. The urinary flow rate signal C when the stream of urine is collected in drops has the greatest impact noise, because impact caused by a water wave when the water (urine) falls in drops is propagated to an entire surface of the water. In FIGS. 7a, 7b and 7c, the urinary flow rate signal D is a signal when the rest of the water in the container is manually introduced.

Figure 8:
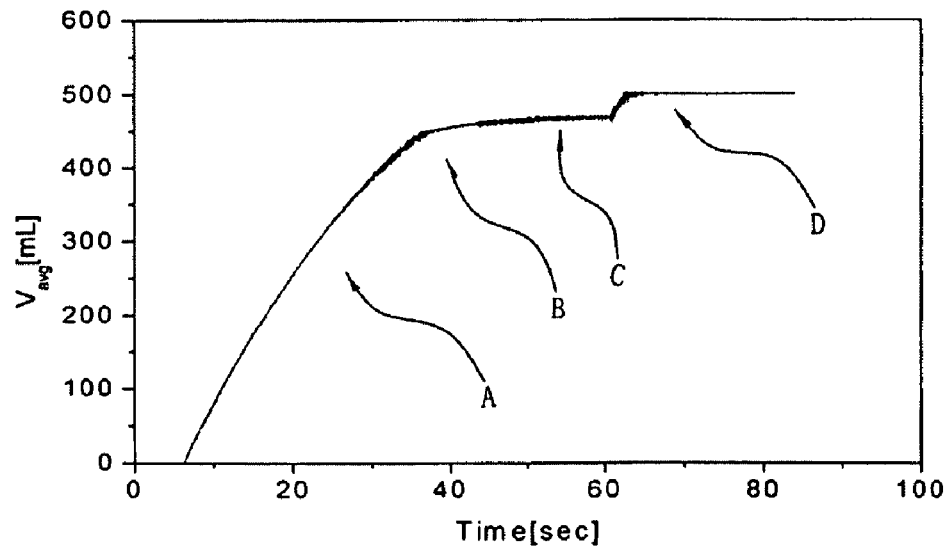
FIG. 8 is a graph depicting the average of three signals of FIGS. 7a, 7b and 7c.

FIG. 8 is a graph depicting the average of three signals of FIGS. 7a, 7b and 7c. It can be found that the impact noise components of A, B, C and D nearly disappear on the whole.

When the three signals are averaged as described above, the impact signal nearly disappear, so that the urinary flow rate of the urine collected into the urinary collecting container can be accurately measured.

More specifically, the three load cells measure an amount of urine collected into the urinary collecting container, and then convert the measured values into the urinary flow rate signals. The urinary flow rate signals are converted into digital signals through a signal-extracting and averaging circuit, which obtains the sum V of $V_A/3$, $V_B/3$ and $V_C/3$ having values of resistance R, and an A/D converting circuit, and then are output through a personal computer (PC) or a microprocessor analyzer, which is interfaced with the A/D converting circuit. Thereby, the accurate urinary flow rate from which the impact noise is minimized can be measured.

Here, the signal-extracting and averaging circuit, the A/D converting circuit, and the PC or microprocessor analyzer are well known in the related art.

As described above, according to an embodiment of the present invention, the urinary flow rate signals are measured by the three load cells, and are averaged to remove the impact noise, so that the urinary flow rate can be accurately measured. Accordingly, the prostatic hypertrophy can be diagnosed in a more convenient and accurate manner.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A method for measuring a urinary flow rate so as to minimize impact noise when prostatic hypertrophy is diagnosed, the method comprising the steps of:
   measuring an amount of urine collected into a container using three load cells;
   extracting and averaging urinary flow rate signals from the measured results;
   removing impact noise from the urinary flow rate signals using the three load cells;
   averaging the flow rate signals obtained from the three load cells;
   converting the averaged flow rate signals into digital signals through an A/D converting circuit; and
   outputting the digital signals using a personal computer or a microprocessor analyzer which is interfaced with the A/D converting circuit.

2. The method as set forth in claim 1, wherein the three load cells are disposed in an equilateral triangular pattern.

3. A system for measuring a urinary flow rate so as to minimize impact noise when prostatic hypertrophy is diagnosed, the system comprising:
   a container configured for collecting urine;
   an upper plate configured for having the container placed thereon;
   a plurality of load cells installed below the upper plate and attached to a bottom plate;
   an extracting and averaging circuit for extracting and averaging urinary flow rate signals from the load cells;
   an A/D converting circuit for receiving the signals from the extracting and averaging circuit, and for performing A/D conversion on the received signals; and
   at least one of a personal computer and a microprocessor analyzer for outputting and displaying the signals from the A/D converting circuit to a user.

4. The system as set forth in claim 3, wherein three load cells are disposed in an equilateral triangular pattern.

* * * * *